(12) United States Patent
Li et al.

(10) Patent No.: US 12,048,549 B1
(45) Date of Patent: Jul. 30, 2024

(54) STREET GREENING QUALITY DETECTION METHOD BASED ON PHYSIOLOGICAL ACTIVATION RECOGNITION

(71) Applicant: SOUTHEAST UNIVERSITY, Nanjing (CN)

(72) Inventors: Zhe Li, Nanjing (CN); Liya Wang, Nanjing (CN); Xiao Han, Nanjing (CN); Jie Li, Nanjing (CN); Qixin Zhang, Nanjing (CN); Mingjing Dong, Nanjing (CN); Mingchen Xu, Nanjing (CN); Shuang Wu, Nanjing (CN); Yi Shi, Nanjing (CN); Haini Chen, Nanjing (CN); Qiaochu Wang, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 0 days.

(21) Appl. No.: 18/565,501

(22) PCT Filed: Apr. 4, 2023

(86) PCT No.: PCT/CN2023/086184
§ 371 (c)(1),
(2) Date: Nov. 29, 2023

(87) PCT Pub. No.: WO2024/098649
PCT Pub. Date: May 16, 2024

(30) Foreign Application Priority Data

Nov. 8, 2022 (CN) .......................... 202211390493.5

(51) Int. Cl.
*G06V 10/00* (2022.01)
*A61B 5/0205* (2006.01)
(Continued)

(52) U.S. Cl.
CPC ............ *A61B 5/378* (2021.01); *A61B 5/0205* (2013.01); *A61B 5/0533* (2013.01); *A61B 5/352* (2021.01);
(Continued)

(58) Field of Classification Search
CPC ............ G06N 3/08; G06N 3/02; G06N 3/042; G06N 3/045; G06N 3/047; G06N 3/082;
(Continued)

(56) References Cited

U.S. PATENT DOCUMENTS 6,627,441 B1 * 9/2003 Attree .................... A01H 4/005
800/298
8,093,182 B2 * 1/2012 Nonomura ............. A01N 43/16
504/100

(Continued)

FOREIGN PATENT DOCUMENTS

| CN | 110111019 A | 8/2019 |
| CN | 111027375 A | 4/2020 |

(Continued)

OTHER PUBLICATIONS

Chen, Feifei, Quantitative Research of Landscape Attraction Based on the Principal Component Analysis Model Using EEG—Case Study of Xinfu Reservoir in Changzhou, China Outstanding Master's Degree Thesis Full Text Database of Engineering Science and Technology II Series, 2022, pp. 21-57.
(Continued)

*Primary Examiner* — Amir Alavi
(74) *Attorney, Agent, or Firm* — Bayramoglu Law Offices LLC

(57) ABSTRACT

A street greening quality detection method based on physiological activation recognition is provided. The street greening quality detection method includes establishing a greening quality factor index system, and obtaining and uniformly
(Continued)

processing street greening images; collecting raw data, and performing reclassification and differential wave processing on the raw data to obtain valid physiological data that can be used for activation feature recognition of greening quality factors; calculating physiological activation feature parameters, training the physiological activation feature parameters by transfer learning fusion to determine importance of physiological activation features, and recognizing weighted average greening activation indexes of the greening quality factors; analyzing weighted average greening activation index data of the greening quality factors to form a street greening quality detection model; and inputting annotated street samples to be analyzed into the street greening quality detection model to obtain annotated results of street greening quality grading detection target data.

20 Claims, 7 Drawing Sheets

(51) Int. Cl.
| | |
|---|---|
| *A61B 5/0533* | (2021.01) |
| *A61B 5/352* | (2021.01) |
| *A61B 5/378* | (2021.01) |
| *A61B 5/397* | (2021.01) |
| *G06N 20/00* | (2019.01) |
| *G06V 10/26* | (2022.01) |
| *G06V 10/764* | (2022.01) |
| *G06V 20/00* | (2022.01) |
| *G06Q 50/26* | (2012.01) |

(52) U.S. Cl.
CPC ............ *A61B 5/397* (2021.01); *G06N 20/00* (2019.01); *G06V 10/26* (2022.01); *G06V 10/764* (2022.01); *G06V 20/39* (2022.01); *A61B 2503/12* (2013.01); *G06Q 50/26* (2013.01)

(58) Field of Classification Search
CPC .... G06N 3/092; G06N 3/0454; G06N 3/0464; G06N 3/0475; G06N 20/00; G06N 20/10; G06V 10/26; G06V 10/764; G06V 20/39; A61B 5/378; A61B 5/397; A61B 5/0205; A61B 5/0533; A61B 2503/12; G06Q 50/26
See application file for complete search history.

(56) References Cited

U.S. PATENT DOCUMENTS

| | | | |
|---|---|---|---|
| 8,546,360 B2 * | 10/2013 | Musson, IV | A01N 57/12 |
| | | | 514/141 |
| 9,758,836 B2 * | 9/2017 | Jin | A01H 3/04 |
| 10,508,394 B1 * | 12/2019 | Chai | E01F 13/02 |
| 11,311,220 B1 | 4/2022 | Al-Saggaf et al. | |
| 11,800,834 B2 * | 10/2023 | Ballew | A01G 2/38 |
| 2006/0070299 A1 * | 4/2006 | Furumura | A01G 9/02 |
| | | | 47/69 |

FOREIGN PATENT DOCUMENTS

| | | |
|---|---|---|
| CN | 112329498 A | 2/2021 |
| CN | 113516638 A | 10/2021 |
| CN | 114334139 A | 4/2022 |
| CN | 114596003 A | 6/2022 |
| CN | 114782821 A | 7/2022 |
| CN | 115063653 A | 9/2022 |
| CN | 115563484 A | 1/2023 |

OTHER PUBLICATIONS

Li Zhe, et al., The Principal Component Quantitative Analysis of Landscape Attraction Based on the EEG Technology—Taking Xuanwu Lake Park of Nanjing as the Example, Chinese Garden, 2021, pp. 60-65, vol. 37, No. 7.

* cited by examiner

STREET GREENING QUALITY DETECTION METHOD BASED ON PHYSIOLOGICAL ACTIVATION RECOGNITION

CROSS REFERENCE TO THE RELATED APPLICATIONS

This application is the national phase entry of International Application No. PCT/CN2023/086184, filed on Apr. 4, 2023, which is based upon and claims priority to Chinese Patent Application No. 202211390493.5, filed on Nov. 8, 2022, the entire contents of which are incorporated herein by reference.

TECHNICAL FIELD

The present invention relates to the field of built environment quality measurement, and in particular, to a street greening quality detection method based on physiological activation recognition.

BACKGROUND

Street greening is one of the components of an urban landscape system, is closely related to people's lives, and plays an indispensable role in the development of built environments. As China's urbanization enters the era of "refined operation", the connotation of renewal of built environment stock is increasingly rich. Street greening, as an important part of human settlement environment construction, is also the most basic landscape unit for urban repair, ecological empowerment, and environmental quality improvement, and is also a suitable construction behavior that meets people's needs for a better life and highlights the quality of a city. For example, in planning and design of urban street greening, measuring and improving the structural form and visual relationship of greening directly affect the level of greening construction, thereby affecting the spatial form, environmental quality, and public vitality of streets.

In recent years, common quality detection methods for built environment greening mostly focus on establishing an evaluation index system based on the visual characteristics of greening images and analyzing changing trends and combined effects of greening elements and their demands for environmental site construction, and produce a series of research results through comparative evaluation on urban environmental samples. Relevant intellectual property achievements include: an automatic recognition method for plant growth quality through static plant image capture, high-quality plant feature extraction, structured storage in time series, and calculation of morphological feature entropy (application number: 201911040562.8); a comprehensive evaluation method for performances of ornamental plant landscape, including establishment of a multi-level performance evaluation system, invocation of information multivariate databases, calculation of weight determination matrices, and generation of stacked bar charts (application number: 201910407314.6); an analysis method for visual comfort of plant landscape, including acquisition of plant image evaluation data, landscape effect threshold scores, analysis on difference in green looking ratio, and calculation of a logistic stepwise regression model (application number: 202210304173.7), etc. Although some progress has been made in the current invention about greening quality, there are still limitations: acquisition of raw data or presentation of final results are still constrained by technical conditions and subjective intentions, manual annotation costs are high, and the speed of data update is unable to cope with the changes and needs of urban high-speed construction; greening quality index systems are mostly based on existing models and frameworks and focus only on a single or a few greening constituent elements, which affects the accuracy and globality of overall environmental quality analysis systems; and acquisition and analysis of greening quality factor parameters in specific plans often rely on experience or evaluation scores, so the operational efficiency, scientificity, and universality remain to be improved.

SUMMARY

To solve the shortcomings mentioned in the background of the invention, the present invention aims to provide a street greening quality detection method based on physiological activation recognition.

The objective of the present invention can be achieved through the following technical solution: A street greening quality detection method based on physiological activation recognition includes the following steps:

establishing a greening quality factor index system according to high-frequency street landscape characteristics, and obtaining and uniformly processing street greening images for greening stimulus physiological experiments;

collecting electroencephalogram (EEG), electrocardiogram (ECG), electrodermogram (EDA) and electromyogram (EMG) raw data stimulated by the street greening images, and performing reclassification and differential wave processing on the raw data according to greening quality factor indexes to obtain valid physiological data that can be used for activation feature extraction of greening quality factors;

calculating EEG, ECG, EDA and EMG physiological activation feature parameters of the greening quality factors according to the obtained valid physiological data, training the physiological activation feature parameters by transfer learning fusion to determine importance of physiological activation features, and recognizing weighted average greening activation indexes of the greening quality factors;

analyzing weighted average greening activation index data of the greening quality factors to form a street greening quality detection model for contrast detection of street greening quality; and inputting annotated street samples to be analyzed into the street greening quality detection model to obtain annotated results of street greening quality grading detection target data.

Preferably, the process of establishing the greening quality factor index system includes the following steps:

collecting statistics on frequencies of street greening structures, plant attributes, visual landscape and the like, selecting high-frequency street greening quality factors, and sorting out constituent elements, typical features and environmental connotations of street greening by a theoretical analysis method, to establish the street greening quality factor index system, where the street greening quality factor index system includes primary element dimensions, secondary variable factors and tertiary factor change form indexes;

acquiring data of built environment street view images, determining street greening scene class images in the street view images by location scene recognition technology, performing feature sampling on single greening quality variable factors of the greening scene class images by image element semantic segmentation technology, and determining clear street greening target images by a square gradient function; and randomly selecting m street greening images from the street greening target images, and performing three phase randomizations on the m street greening images to obtain 3*m random phase images and form an experimental stimulus image library; dividing all experimental stimulus images in the experimental stimulus image library into n groups through inter-group experiments, and playing the experimental stimulus images at a random inter-group and same frequency in a laboratory environment to obtain EEG, ECG, EDA, EMG and trigger signals of corresponding data segments of the images in real time.

Preferably, the primary element dimension indexes of the greening quality factor index system include greening structure, plant texture, line of sight relationship, and landscape characteristics; the secondary variable factor indexes are extensions of the primary greening quality elements; and the tertiary factor change form indexes are manifestations of variable factors, and factor features of greening quality are sampled through the built environment street view images.

Preferably, the process of collecting EEG, ECG, EDA and EMG raw data stimulated by the street greening images, and performing reclassification and differential wave processing on the raw data according to greening quality factor indexes includes the following steps:

capturing raw data of each street greening target image when stimulated, and classifying raw data segments representing a same greening quality variable factor into one class according to markers recorded by the trigger signals, where each class of data segments reflects EEG, ECG, EDA and EMG changes of subjects under the influence of a variable factor; performing baseline correction, bandpass filtering, average reference processing, independent component analysis (ICA), noise reduction and artifact removal on the raw data segments, and correcting signal offsets by empirical mode decomposition (EMD), so as to solve average amplitudes and differential waves of non-stimulus state electrical signals caused by greening quality factor stimulus states; and analyzing the amplitudes and phase images of differential waveforms by Hanning windowing, fast Fourier transform and wavelet transform, and extracting β and α frequency bands of five EEG differential wave leads PZ, P4, P5, O1, OZ, and O2, low-frequency and high-frequency bands of ECG differential waves at R-R intervals, high-frequency bands of EMG differential waves after full-wave rectification, and a normalized conductivity GSR of EDA differential waves within an exposure time window of the street greening target images, so as to calculate power spectral densities of the EEG, ECG and EMG frequency bands and a first-order difference of the EDA conductivity, to obtain valid physiological data for physiological activation feature recognition of the greening quality factors.

Preferably, the process of calculating EEG, ECG, EDA and EMG physiological activation feature parameters of the greening quality factors according to the obtained valid physiological data, training the physiological activation feature parameters by transfer learning fusion to determine importance of physiological activation features, and recognizing weighted average greening activation indexes of the greening quality factors includes the following steps:

superposing and averaging physiological data of each class of greening quality factors according to the obtained valid physiological data, calculating the EEG, ECG, EDA and EMG physiological activation feature parameters of the greening quality factors respectively, and normalizing the calculated EEG, ECG, EDA and EMG physiological activation feature parameters of the greening quality factors;

obtaining a physiological activation feature vector $A^{(m)}=\{a_x^{(m)}\}$, ($x=1, 2, \ldots, N$, $m=1, 2, \ldots, J$) of the greening quality factors from the normalized EEG, ECG, EDA and EMG physiological activation feature parameters of the greening quality factors, where $a_i^{(m)}$ represents an $m^{th}$ physiological activation feature of an $x^{th}$ class of greening quality factor objects; constructing a physiological activation feature importance determination matrix $B=\{b_{ij}\}$, where $b_{ij}$ represents an importance degree ratio of an $i^{th}$ activation feature dimension to an $j^{th}$ activation feature dimension; consequently, obtaining a weight vector $w^*=[w_1, w_2, \ldots, w_j]$ of each feature; and fusing the physiological activation features by transfer learning TLDA, using 70% of the samples as a source domain dataset and remaining 30% as a target domain dataset, obtaining marker activation values of source domain street greening target images, performing sparse self-encoding on the physiological activation feature vector $A^{(m)}$ and the marker activation value Y of the greening quality factors, determining the number of neurons q ($q<m$) in a self-encoder, introducing $A^{(m)}$ into a neural network, and assigning physiological activation feature weights after neural network training to obtain an ensemble vector E of fused features and a weighted average greening activation index O corresponding to E, as follows:

$$O = \frac{1}{4}\sum_{i=1}^{m}\frac{\omega_i}{\sum_{j=1}^{m}\omega_j}o_k$$

where $\omega_i$ represents a weight of each source domain, namely, a modulus of a similarity vector in the ensemble vector E, and $o_k$ represents a predicted activation degree of a $k^{th}$ class of greening quality factors.

Preferably, the process of calculating EEG, ECG, EDA and EMG physiological activation feature parameters of the greening quality factors includes the following steps:

calculating an EEG activation feature parameter $A_{EEG}$ of the greening factor object by the following formula:

$$A_{EEG} = \frac{P_{\beta,x}}{P_{\alpha,x}}$$

where $P_{\beta,x}$ and $P_{\alpha,x}$ represent relative average power of the five leads PZ, P4, P5, O1, OZ, and O2 with respect to the β and α bands of the currently calculated greening quality factor object x;

calculating an ECG activation feature parameter $A_{ECG}$ of the greening factor object by the following formula:

$$A_{ECG} = \frac{P_{LF,x}}{P_{HF,x}}$$

where $P_{LF,x}$ represents a power value of an ECG low-frequency component of the greening quality factor x, and $P_{HF,x}$ represents a power value of an ECG high-frequency component of the greening quality factor x;

calculating an EDA activation feature parameter $A_{EDA}$ of the greening factor object by the following formula:

$$A_{EDA} = \frac{1}{2}(t_{peak} - t_{onset}) * (s_{peak} - s_{onset})$$

where $t_{peak}$ and $t_{onset}$ represent a peak and beginning of ΔGSR rise time during stress response, $s_{peak}$ and $s_{onset}$ represent a peak and beginning of a ΔGSR amplitude value during stress response, and $A_{EDA}$ represents activation of 10% higher than a baseline during GSR stress response;

calculating an EMG activation feature parameter $A_{EMG}$ of the greening factor object by the following formula:

$$A_{EMG} = \frac{1}{2}\int_0^{+\infty} P_{EMG,x} df$$

where $P_{EMG,x}$ represents a power spectral density function of EMG signals of the currently calculated greening quality factor object x, and f represents a frequency of the EMG signals;

normalizing the physiological activation feature parameters of each greening quality factor and introducing the following calculation formula:

$$A_{Normalized} = \left(\frac{A(i) - A_{min}}{A_{max} - A_{min}}\right) \times 100$$

where $A(i)$ represents the $i^{th}$ activation feature parameter, $A_{min}$ and $A_{max}$ represent a minimum value and a maximum value of the activation feature parameters, and $A_{Normalized}$ represents normalized activation feature parameters.

Preferably, the process of analyzing weighted average greening activation index data of the greening quality factors to form a street greening quality detection model includes the following steps:

obtaining a weighted average greening activation index of each class of greening quality factors, checking the weighted average greening activation index data of the greening quality factors by KMO measure of sampling adequacy and Bartlett's test of sphericity, where when KMO value >0.6 and sphericity test adjoint probability P value≤0.01, it is considered that factor variables are strongly correlated and are suitable for further analysis on the greening factor objects;

calculating a cumulative variance contribution rate $M_K$ of latent principal components of an initial greening quality variable matrix $X=\{x_{ij}\}$, (i=1, 2, 3, ..., m; j=1, 2, 3, ..., n), and selecting latent principal components of greening quality at $M_K \geq 80\%$ as follows:

$$M_K = \sum_{i=1}^{k} \frac{\varepsilon_{ij}}{\sqrt{\eta_j}}$$

where $x_{ij}$ represents a $j^{th}$ greening quality variable factor of an $i^{th}$ sample; $\varepsilon_{ij}/\sqrt{\eta_j}$ represents a $k^{th}$ latent principal component of the greening quality, $\varepsilon_{ij}$ represents factor load of a $j^{th}$ latent principal component of an $i^{th}$ variable factor, and $\eta_{ij}$ represents a characteristic root of the $j^{th}$ latent principal component;

extracting the first k latent principal components to detect the street greening quality, and calculating a weight $w_i'$ of a single greening quality variable factor according to the related coefficient matrices and the variance contribution rate as follows:

$$w_i' = \left|\sum_{i=1}^{n}\left(\frac{\varepsilon_{ij}}{\sqrt{\eta_j}} * \gamma_j\right)\right|/\gamma_j$$

where $\gamma_j$ represents a variance contribution rate corresponding to the $j^{th}$ latent principal component of the greening quality, and the larger the $w_i'$, the greater the importance of the greening quality variable factor; and forming the street greening quality detection model according to weight coefficients of the greening quality variable factors, which is used for contrast detection of the street greening quality:

$$G = \lambda_1 x_1 + \lambda_2 x_2 + \lambda_3 x_3 + \ldots + \lambda_j x_j$$

where $\lambda_1$ represents an influence coefficient of the $i^{th}$ factor, and $x_j$ represents greening activation index data of a $j^{th}$ re-extracted factor.

Preferably, the process of inputting annotated street samples to be analyzed into the street greening quality detection model to obtain annotated results of street greening quality grading detection target data includes the following steps:

collecting physiological data of J subjects with respect to I street greening images of N street samples to obtain an initial greening quality variable matrix $Z=\{z_{ij}\}$, (i=1, 2, 3, ..., M; j=1, 2, 3, ..., N) of M greening quality variable factors of the N street samples, and annotating the EEG, ECG, EDA and EMG physiological activation feature parameters of the N street samples in classes according to the classes of the greening quality variable factor indexes;

establishing a greening activation relationship fusion model among the EEG, ECG, EDA and EMG activation feature parameters, generating a fused greening activation index of the J subjects with respect to the street greening quality variable factors, setting confidence of the greening activation index data within a [0, 1] interval, and annotating the variable factors of the street samples with activation degrees;

presetting greening quality detection conditions, dividing the street greening quality into four levels $G_1$, $G_2$, $G_3$, and $G_4$, and assigning hierarchical values to the element dimensions of the street samples from high to low, to rank the greening quality of the street samples;

$$C_i = \begin{cases} 4, x_{ij} \in [\bar{x} + 0.5\sigma, x_{max}] \\ 3, x_{ij} \in [\bar{x}, \bar{x} + 0.5\sigma) \\ 2, x_{ij} \in [\bar{x} - 0.5\sigma, \bar{x}) \\ 1, x_{ij} \in [x_{min}, \bar{x} - 0.5\sigma) \end{cases}$$

where $x_{ij}$ represents greening activation annotation data of an $j^{th}$ element dimension at an $i^{th}$ location, $\bar{x}$ represents an average value of greening activation degrees of all samples, σ represents a standard deviation of the greening activation degrees of all samples, and $C_i$ represents a level of assigned greening quality of the $i^{th}$ element dimension; and inputting the annotated street samples into the street greening quality detection model, obtaining activation degrees of the element dimensions of the street samples one by one through the calculated greening variable factors and element dimensions, on this basis, reassigning the greening quality of each element dimension with reference to the greening quality grading detection conditions, and performing weighted superposition on the dimension weights of the greening quality elements to form and annotate dimensionless greening quality values of the street samples;

$$Y = \sum_{i=1}^{n} w_i^* C_i'$$

where Y represents the greening quality values of the street samples, $w_i^*$ represents a weight of a $i^{th}$ element dimension, and $C_i'$ represents level assignment of greening quality at the $i^{th}$ element dimension.

Preferably, a device includes:
one or more processors; and
a memory, configured to store one or more programs, where
when the one or more programs are executed by the one or more processors, the one or more processors are enabled to implement the street greening quality detection method based on physiological activation recognition as described above.

Preferably, a storage medium including computer executable instructions that, when executed by a computer processor, are used to perform the street greening quality detection method based on physiological activation recognition as described above.

Beneficial effects of the present invention are as follows:
1. In response to insufficient comprehensive analysis on greening feature data of composite built environments, the present invention employs a theoretical analysis method to sort out constituent elements, typical features and environmental connotations of street greening, establishes a greening quality factor index system including element dimensions, variable factors and specific forms of factor changes, and focuses on correlation data between physiological activation of street greening and street greening quality, thereby achieving overall analysis on multi-dimensional data of greening factor objects, and improving the speed and efficiency of street greening quality detection.

2. In response to the shortcomings of cumbersome collection, significant fluctuation amplitude, long processing cycle, and the like of environmental activation data, the present invention recognizes multi-source physiological signals as physiological activation features with high accuracy, and performs fusion training on a plurality of physiological activation features by transfer learning TLDA to obtain quantifiable greening activation indexes of built environment greening images, thereby improving the efficiency of data collection for greening activation analysis and the temporal and spatial accuracy of feature fusion analysis, overcoming social approval bias interference, and promoting scientific, objective, and standardized development of basic data acquisition for built environment street greening.

3. In response to strong subjectivity and high cost of detection result annotation, emphasis on early calculation methods, and lack of exploration for later application, the present invention fuses the physiological activation relationship between environmental site samples on hierarchical greening quality test results, uses greening quality factor objects as data sets, and presets greening quality grading detection conditions, thereby improving the generalization ability of the street greening quality detection model, then providing application approaches for improvement on greening quality and evidence-based design of built environments, and promoting refined development of the built environments.

BRIEF DESCRIPTION OF THE DRAWINGS

In order to explain the embodiments of the present invention or the technical solutions in the prior art more clearly, the accompanying drawings required for the description of the embodiments or the prior art will be introduced simply. Apparently, those skilled in the art can obtain other drawings based on these drawings without any creative effort.

DETAILED DESCRIPTION OF THE EMBODIMENTS

The technical solutions in the embodiments of the present invention will be clearly and completely described below with reference to the accompanying drawings in the embodiments of the invention. Apparently, the described embodiments are only some of the embodiments of the present invention, no all of them. All other embodiments obtained by those of ordinary skill in the art based on the embodiments of the present invention without any creative effort shall fall within the protection scope of the present invention.

Figure 1:
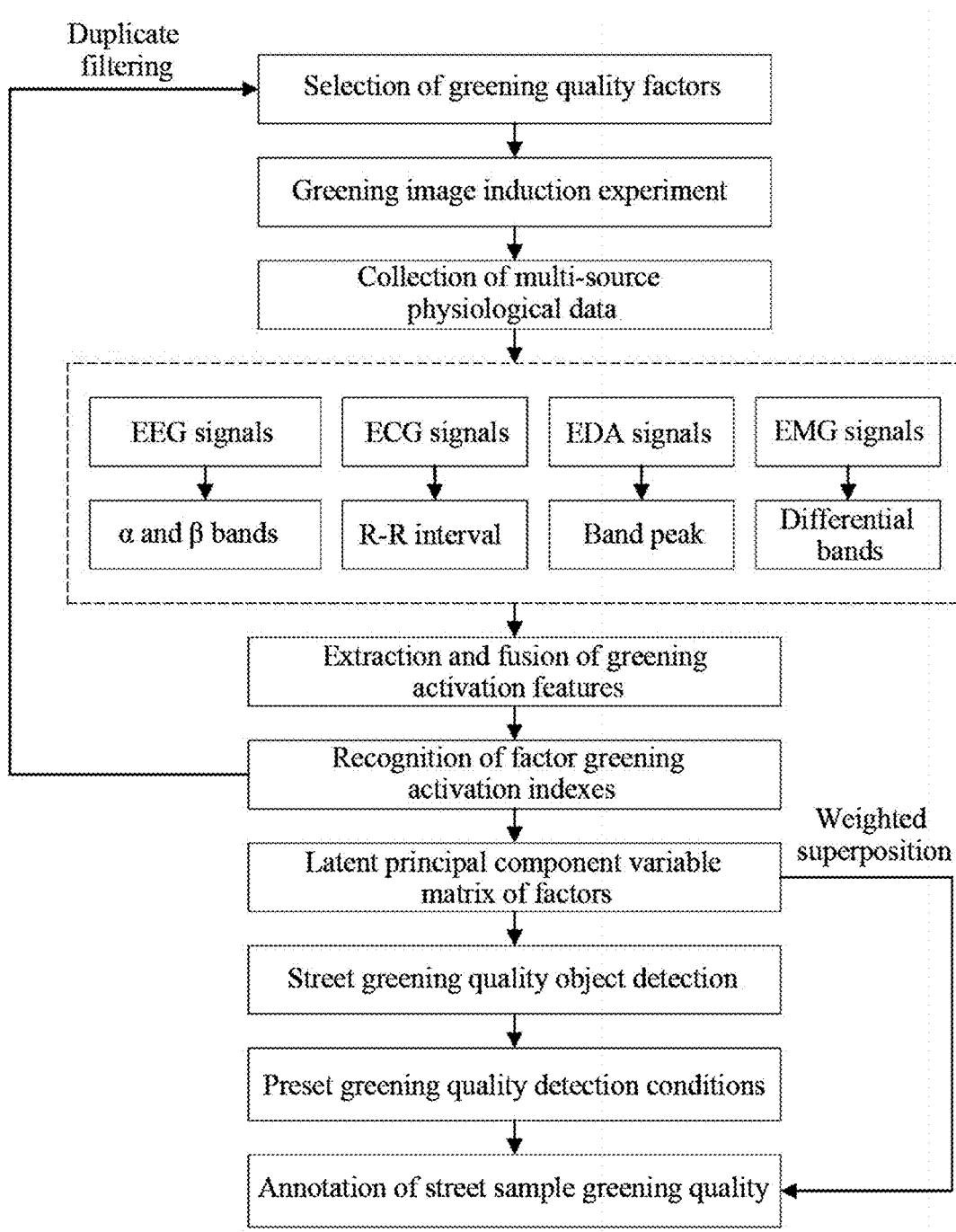
FIG. 1 is a flowchart of a street greening quality detection method based on physiological activation recognition of the present invention.
Figure 2A:
FIGS. 2A-2D show a feedback graph of superimposed average physiological activation features of subjects according to an embodiment of the present invention.
Figure 2B:
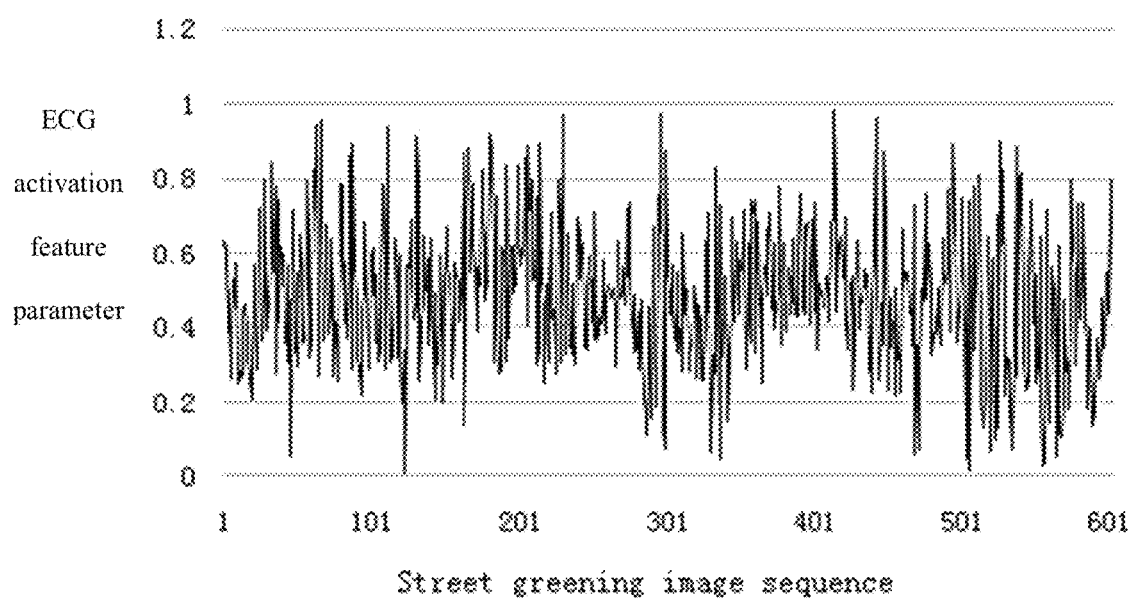
Figure 2C:
Figure 2D:

As shown in FIG. 1, a street greening quality detection method based on physiological activation recognition includes the following steps:

(1) A greening quality factor index system is established according to high-frequency street landscape characteristics, and street greening images are obtained and uniformly processed for greening stimulus physiological experiments:

(1-1) Statistics on frequencies of street greening structures, plant attributes, visual landscape and the like in existing literature are collected, high-frequency street greening quality factors are selected, and constituent elements, typical features and environmental connotations of street greening are sorted out by a theoretical analysis method, to establish the street greening quality factor index system, including primary element dimensions, secondary variable factors and specific tertiary factor change form indexes, as shown in Table. 1. The primary element dimensions include greening structure, plant texture, line of sight relationship, and landscape characteristic. The secondary variable factor indexes are extensions of the primary greening quality elements, including 18 street greening variable factors such as green form, greening composition, and green looking ratio. The tertiary indexes are manifestations of the variable factors, and factor features of greening quality are sampled through the built environment street view images.

performed on variable factors of the street greening scene class images by using an ADE20K-CNN dataset and a Cascade DilatedNet semantic segmentation model. The images with a green visual ratio >5% are used as the street greening target images for next analysis and processing.

80 typical street greening target images with 3-5 different change forms are selected for each greening quality factor, and 3*80=240 random street greening phase images after three phase randomizations are obtained to form the experimental stimulus image library. The experimental stimulus images are divided into 2 groups for inter-group experiments, with each image cycled three times and flashed for 3000 ms at a frequency of 10 Hz and with a resting state of

TABLE 1

Street greening quality factor index system

| Element dimension | Variable factor | Specific change forms of indexes | | |
|---|---|---|---|---|
| Greening structure | Green pattern (GP) | Regular | Slightly natural | Natural |
| | Green class (GC) | ≤2 classes | 3-5 classes | >5 classes |
| | Green combination (GP) | Shrub | Arbor | Arbor and shrub |
| | Green form (GF) | Linear, group, cluster, coupled, and isolated planting | | |
| | View method (GM) | Flower mirror | Flower bed | Three-dimensional greening |
| Plant texture | Green color (GO) | Monochromatic system | Contrast two colors | Composite colors |
| | Green situation (GS) | Poor | Ordinary | Good |
| | Plant trait (BF) | Branches | Contour | Branches and leaves |
| | Plant luster (BL) | Poor | Ordinary | Good |
| | Seasonal ratio (SR) | ≤30% | (30, 60] % | (60 100] % |
| Line of sight relationship | Green visual ratio (GV) | (5, 30] % | (30, 60] % | (60 100] % |
| | Intervisibility (VA) | ≤10% | (10, 40] % | (40 100] % |
| | Green density (DC) | ≤30% | (30, 60] % | (60 100] % |
| | Green height (GH) | ≤0.6 m | (0.6, 1.5]m | >1.5 m |
| Landscape characteristics | Oddity (ODD) | Low price | Moderate price | High price |
| | Awareness (ARE) | Poor | Ordinary | Good |
| | Ancient wood ratio (PAW) | ≤10% | (10, 40] % | (40 100] % |
| | Tree age (GAT) | ≤10 years | (10, 30) years | (30, 100] years |

(1-2) Data of built environment street view images are acquired, street greening scene class images in the street view images are determined by location scene recognition technology, feature sampling is performed on single greening quality variable factors of the greening scene class images by image element semantic segmentation technology, and clear street greening target images are determined by a square gradient function; and (1-3) m street greening images are randomly selected from the experimental materials, and three phase randomizations are performed on the m street greening images to obtain 3*m random phase images and form an experimental stimulus image library. All experimental stimulus images are divided into n groups through inter-group experiments, and played at a random inter-group and same frequency in a laboratory environment to obtain EEG, ECG, EDA, EMG and trigger signals of corresponding data segments of the images in real time.

In this embodiment, a Place365-CNN model dataset and a ResNet152-Hybrid1365 ascene classification model are selected as street greening scene detection tools. The images sorted in the top three places in detection labels and related to the semantics of greening elements are determined as street greening scene class images. Feature sampling is 3000 ms between the images. When the experimental stimulus images are played, markers are sent to a physiological oscilloscope to record and collect raw data of EEG, ECG, EDA, EMG and oscilloscope triggered signal changes in real time during playback of each image. A total of 320 raw data segments are captured.

(2) EEG, ECG, EDA and EMG raw data stimulated by the street greening images are collected, and reclassification and differential wave processing are performed on the raw data according to greening quality factor indexes to obtain valid physiological data that can be used for activation feature extraction of greening quality factors;

(2-1) Raw data of each street greening target image when stimulated are captured, and raw data segments representing a same greening quality variable factor are classified into one class according to markers recorded by the trigger signals, where each class of data segments reflects EEG, ECG, EDA and EMG changes of subjects under the influence of a variable factor. Baseline correction, bandpass filtering, average reference processing, independent component analysis (ICA), noise reduction and artifact removal are performed on the raw data segments, and signal offsets are corrected by empirical mode decomposition (EMD), so as to solve average amplitudes and differential waves of non-stimulus state electrical signals caused by greening quality factor stimulus states; and (2-2) The amplitudes and phase images of differential waveforms are analyzed by Hanning windowing, fast Fourier transform and wavelet transform, and (8-12 Hz) β and (14-30 Hz) α frequency bands of five EEG differential wave leads PZ, P4, P5, O1, OZ, and O2, low-frequency (LF: 0.04-0.15 Hz) and high-frequency (LF: 0.15-0.4 Hz) bands of ECG differential waves at R-R intervals, high-frequency (MF: 50-150 Hz) bands of EMG differential waves after full-wave rectification, and a normalized conductivity GSR of EDA differential waves within an exposure time window of the street greening target images are extracted, so as to calculate power spectral densities of the EEG, ECG and EMG frequency bands and a first-order difference of the EDA conductivity, to obtain valid physiological data for physiological activation feature recognition of the greening quality factors.

In this example, experimental data of a total of 65 subjects are collected to obtain 61 groups of valid data. The sampling frequency of the signals is 500 Hz. The baseline correction, noise reduction, artifact removal, filtering, independent component analysis (ICA), and signal offset correction pre-processing of the raw data are completed on a Matlab platform by using software packages such as ECGLab, LedaLab, and HRVAS. A resistance value of each lead electrode in EEG is 10 kΩ or below. A size of the Hanning window is set to 25 ms, and the wavelet transform is Daubechies db2. EEG, ECG, EDA and EMG signal change data from first 2000 ms to last 5000 ms of street greening target image stimulus are captured, and then differential wave analysis is performed on the reclassified signal change data according to the 18 classes of greening quality factors.

(3) EEG, ECG, EDA and EMG physiological activation feature parameters of the greening quality factors are calculated according to the obtained valid physiological data, the physiological activation feature parameters are trained by transfer learning fusion to determine importance of physiological activation features, and weighted average greening activation indexes of the greening quality factors are recognized;

(3-1) Physiological data of each class of greening quality factors are superposed and averaged according to the valid physiological data obtained in step (2-2) after the street greening factors are treated, and the EEG, ECG, EDA and EMG physiological activation feature parameters (as shown in FIGS. 2A-2D) of the greening quality factors are calculated respectively. Specific steps are as follows:

(3-1-1) An EEG activation feature parameter $A_{EEG}$ of a greening factor object is calculated by the following formula:

$$A_{EEG} = \frac{P_{\beta,x}}{P_{\alpha,x}}$$

where $P_{\beta,x}$ and $P_{\alpha,x}$ represent relative average power of the five leads PZ, P4, P5, O1, OZ, and $P_2$ with respect to the β and α bands of the currently calculated greening quality factor object x, and the larger the value of $A_{EEG}$, the higher the degree of activation of a brain visual area by street greening;

(3-1-2) An ECG activation feature parameter $A_{ECG}$ of the greening factor object is calculated by the following formula:

$$A_{ECG} = \frac{P_{LF,x}}{P_{HF,x}}$$

where $P_{LF,x}$ represents a power value of an ECG low-frequency component of the greening quality factor x, $P_{HF,x}$ represents a power value of an ECG high-frequency component of the greening quality factor x, and the larger the value of $A_{ECG}$, the more active the sympathetic nerve, that is, the higher the degree of activation by street greening;

(3-1-3) An EDA activation feature parameter $A_{EDA}$ of the greening factor object is calculated by the following formula:

$$A_{EDA} = \tfrac{1}{2}(t_{peak} - t_{onset}) * (s_{peak} - s_{onset})$$

where $t_{peak}$ and $t_{onset}$ represent a peak and beginning of ΔGSR rise time during stress response, $s_{peak}$ and $s_{onset}$ represent a peak and beginning of a ΔGSR amplitude value during stress response, $A_{EDA}$ represents activation of 10% higher than a baseline during GSR stress response, and the larger the value of $A_{EDA}$, the higher the activation energy for street greening;

(3-1-4) An EMG activation feature parameter $A_{EMG}$ of the greening factor object is calculated by the following formula:

$$A_{EMG} = \frac{1}{2}\int_0^{+\infty} P_{EMG,x} \, df$$

where $P_{EMG,x}$ represents a power spectral density function of EMG signals of the currently calculated greening quality factor object x, f represents a frequency of the EMG signals, and the larger the value of $A_{EMG}$, the higher the activation energy for street greening;

In order to eliminate individual differences among the subjects, the physiological activation features of each greening quality factor are normalized and the following calculation formula is introduced:

$$A_{Normalized} = \left(\frac{A(i) - A_{min}}{A_{max} - A_{min}}\right) \times 100$$

where $A(i)$ represents the $i^{th}$ activation feature parameter, $A_{min}$ and $A_{max}$ represent a minimum value and a maximum value of the activation feature parameters, and $A_{Normalized}$ represents normalized activation feature parameters;

(3-2) A physiological activation feature vector $$A^{(m)} = \{a_x^{(m)}\},$$

Figure 3:
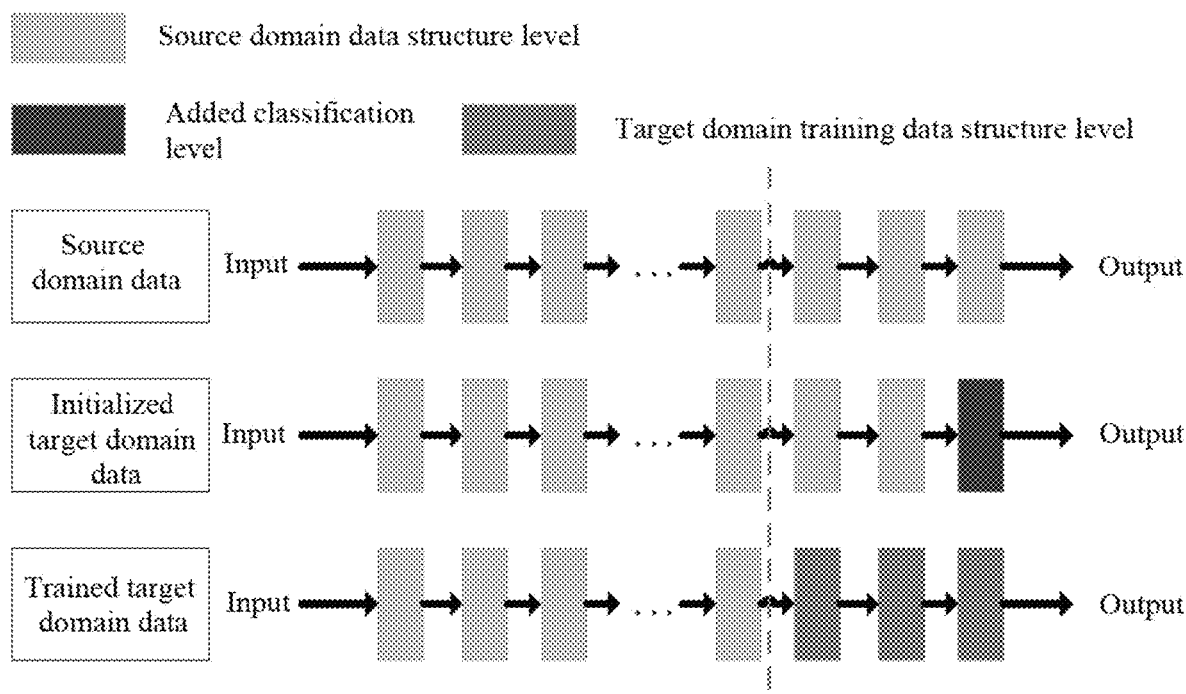
FIG. 3 is a diagram of a fused structure of physiological activation features according to an embodiment of the present invention.

(x=1, 2, ..., N, m=1, 2, ..., J) of the greening quality factors is obtained from the normalized EEG, ECG, EDA and EMG physiological activation feature parameters of the greening quality factors, where $a_i^{(m)}$ represents an $m^{th}$ physiological activation feature of an $x^{th}$ class of greening quality factor objects. A physiological activation feature importance determination matrix B={$b_{ij}$} is constructed, where $b_{ij}$ represents an importance degree ratio of an $i^{th}$ activation feature dimension to an $j^{th}$ activation feature dimension; and consequently, a weight vector w*=[$w_1, w_2, \ldots, w_j$] of each feature is obtained;

(3-3) The physiological activation features are fused by transfer learning TLDA (as shown in FIG. 3), 70% of the samples are used as a source domain dataset, remaining 30% are used as a target domain dataset, marker activation values of source domain street greening target images are obtained, sparse self-encoding is performed on the physiological activation feature vector $A^{(m)}$ and the marker activation value Y of the greening quality factors, the number of neurons q (q<m) in a self-encoder is determined, $A^{(m)}$ is introduced into a neural network, and physiological activation feature weights are assigned after neural network training to obtain an ensemble vector E of fused features and a weighted average greening activation index O corresponding to E, as follows:

$$O = \frac{1}{4}\sum_{i=1}^{m} \frac{\omega_i}{\sum_{j=1}^{m}\omega_j} o_k$$

where $\omega_i$ represents a weight of each source domain, namely, a modulus of a similarity vector in the ensemble vector E, and $o_k$ represents a predicted activation degree of a $k^{th}$ class of greening quality factors.

In this example, EEG signals of the five leads PZ, P4, P5, O1, OZ, and O2 are collected, so EEG has five features. Besides, 2 EDA features, 1 EEG feature, and 1 EMG feature are added, and a total of 9 physiological activation features are collected. For the setting of the activation degree Y of the source domain marker, the environmental activation degree of an SAM scale is used as a determination index. Four transfer learning models are trained according to the EEG, ECG, EDA and EMG physiological activation features. A sigmoid activation function is used for the models, weight parameters of the model are optimized by gradient descent SGD, and fusion models are evaluated by means of balanced F score F1-score and accuracy (as shown in Table 2). After training, the accuracy of the EEG+ECG+EDA+EMG model is the highest, with physiological activation feature weights of 44.2%, 35.47%, 12.16%, and 8.17%.

TABLE 2

Contrast of fusion results of physiological activation features

| Fused features | Accuracy (%) | F1-score |
|---|---|---|
| EEG | 86.47 | 0.8634 |
| EEG + heart rate | 91.04 | 0.9043 |
| EEG + heart rate + EDA | 91.89 | 0.9125 |
| EEG + heart rate + EDA + EMG | 92.47 | 0.9323 |

(4) Weighted average greening activation index data of the greening quality factors are analyzed to form a street greening quality detection model for contrast detection of street greening quality (4-1) A weighted average greening activation index of each class of greening quality factors is obtained, the weighted average greening activation index data of the greening quality factors are checked by KMO measure of sampling adequacy and Bartlett's test of sphericity, where when KMO value >0.6 and sphericity test adjoint probability P value≤0.01, it is considered that factor variables are strongly correlated and are suitable for further analysis on the greening factor objects;

(4-2) A cumulative variance contribution rate $M_K$ of latent principal components of an initial greening quality variable matrix X={$x_{ij}$}, (i=1, 2, 3, ..., m; j=1, 2, 3, ..., n) is calculated, and latent principal components of greening quality at $M_K$≥80% are selected as follows:

$$M_K = \sum_{i=1}^{k} \frac{\varepsilon_{ij}}{\sqrt{\eta_j}}$$

where x represents a $j^{th}$ greening quality variable factor of an $i^{th}$ sample; $\varepsilon_{ij}/\sqrt{\eta_j}$ represents a $k^{th}$ latent principal component of the greening quality, $\varepsilon_{ij}$ represents factor load of a $j^{th}$ latent principal component of an $i^{th}$ variable factor, and $\eta_{ij}$ represents a characteristic root of the $j^{th}$ latent principal component;

(4-3) The first k latent principal components are extracted to detect the street greening quality, and a weight $w_i'$ of a single greening quality variable factor is calculated according to the related coefficient matrices and the variance contribution rate as follows:

$$w_i' = \left|\sum_{1}^{n}\left(\frac{\varepsilon_{ij}}{\sqrt{\eta_j}} * \gamma_j\right)\right|/\gamma_j$$

where $\gamma_j$ represents a variance contribution rate corresponding to the $j^{th}$ latent principal component of the greening quality, and the larger the $w_i'$, the greater the importance of the greening quality variable factor; and (4-4) The street greening quality detection model for contrast detection of the street greening quality is formed according to the factor weight coefficients. The model reflects main factors that affect the greening quality and their contribution rates to the greening quality, specifically:

$$G=\lambda_1 x_1+\lambda_2 x_2+\lambda_3 x_3+ \ldots +\lambda_j x_j$$

where $\lambda_1$ represents an influence coefficient of the $i^{th}$ factor, and $x_j$ represents greening activation index data of a $j^{th}$ re-extracted factor.

Figure 4A:
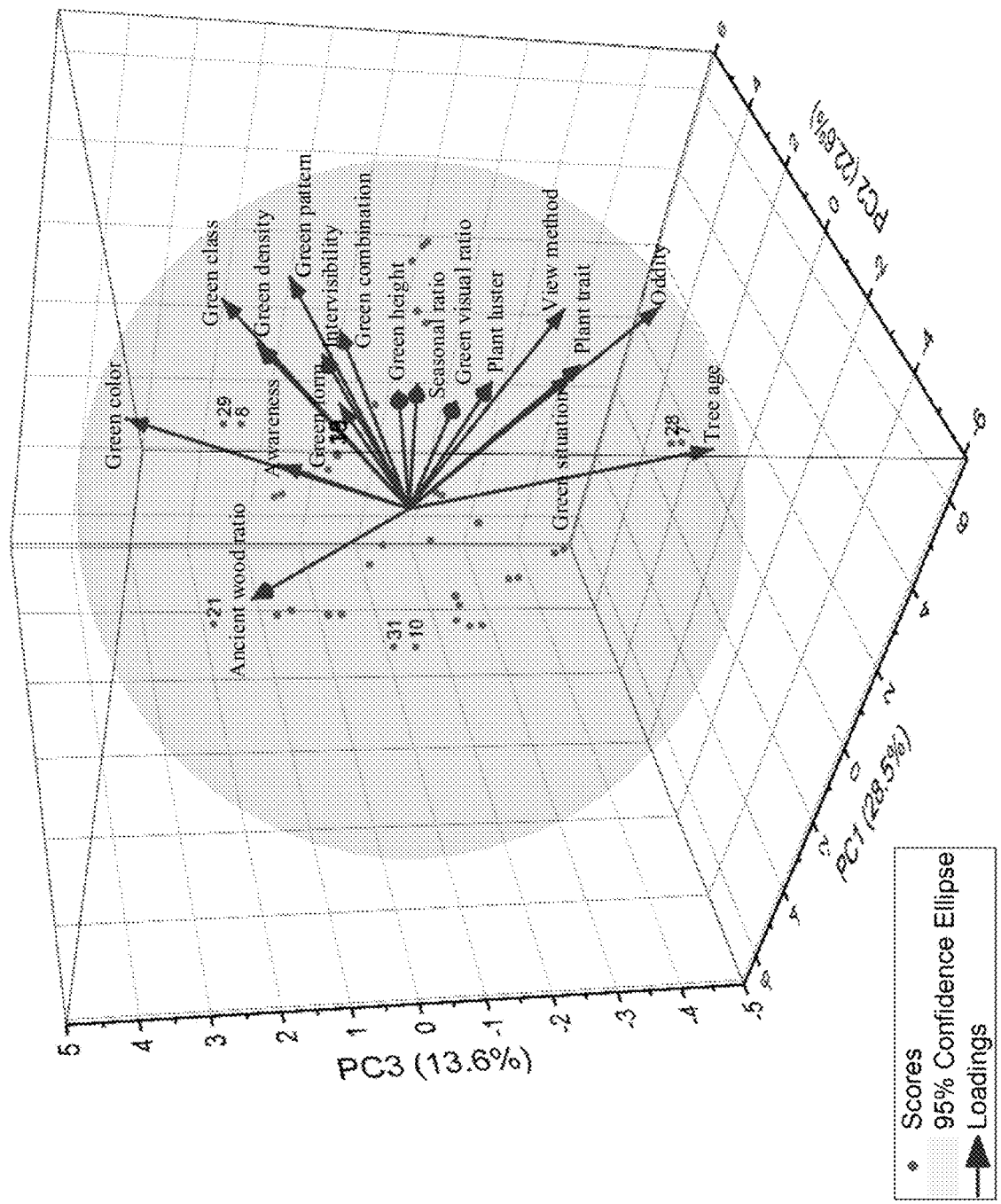
FIGS. 4A-4B show a diagram showing a relationship between latent principal components of greening quality according to an embodiment of the present invention.
Figure 4B:
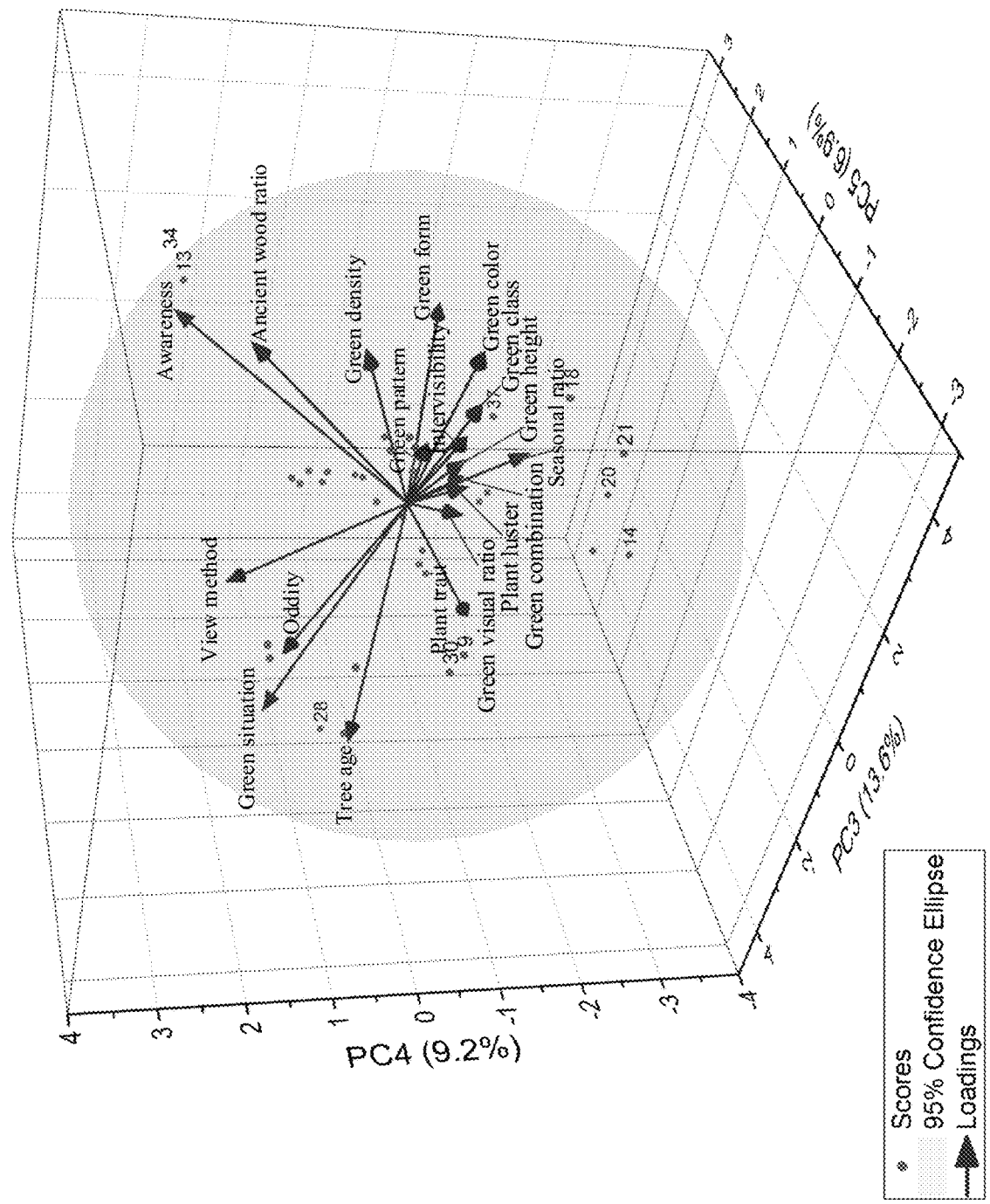
Figure 5:
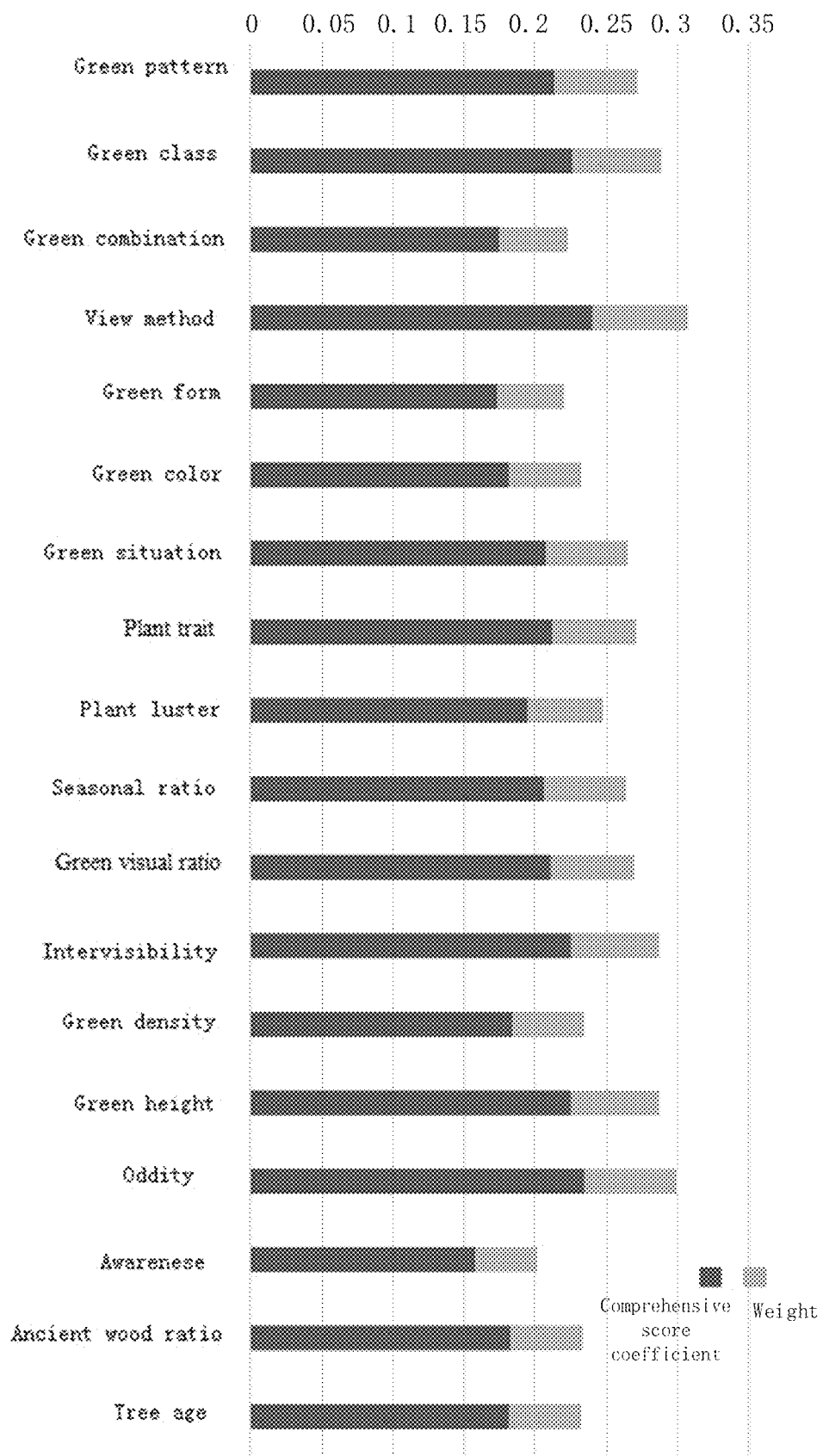
FIG. 5 is a distribution diagram of influence weights and comprehensive score coefficients of greening quality factors according to an embodiment of the present invention.

In this example, the initial greening quality variable matrix is constructed with an overall activation degree of a street greening environment as a dependent variable and the greening quality factor greening activation data as independent variables. After KMO and Bartlett's test of sphericity, the KMO sampling adequacy of the variable matrix is 0.610>0.6, and the adjoint probability P value of the Bartlett's test is 0.000≤0.01, so the two satisfy conditions and can be further analyzed. Latent principal components are extracted from the greening quality factors to obtain 5 new variables that are independent of each other and include initial factor information, the obtained explanatory total variance is 80.782%, which is more than 80% (as shown in Table 3), and a diagram showing a relationship between latent principal components of greening quality is obtained accordingly (as shown in FIGS. 4A-4B). A latent component factor coefficients (as shown in Table 4) and influence weight (as shown in FIG. 5) of each initial greening quality variable factor are obtained according to step (4-3), and the influence weights of all the greening quality factors are distributed between 5% and 7%, with the view method (GM) having the greatest impact on the greening quality.

TABLE 3

Explanation on total variance of latent principal components of greening quality

| Component Serial number | Initial eigenvalue | | | Sum of squares of extracted load | | |
|---|---|---|---|---|---|---|
| | Total | Variance percentage | Cumulative/% | Total | Variance percentage | Cumulative/% |
| 1 | 5.132 | 28.513 | 28.513 | 5.132 | 28.513 | 28.513 |
| 2 | 4.066 | 22.586 | 51.1 | 4.066 | 22.586 | 51.1 |
| 3 | 2.446 | 13.591 | 64.691 | 2.446 | 13.591 | 64.691 |
| 4 | 1.662 | 9.232 | 73.922 | 1.662 | 9.232 | 73.922 |
| 5 | 1.235 | 6.86 | 80.782 | 1.235 | 6.86 | 80.782 |

TABLE 4

Matrix of latent principal component score coefficients of greening quality

| Variable factor | Latent principal component | | | | |
|---|---|---|---|---|---|
| | 1 | 2 | 3 | 4 | 5 |
| Green pattern (GP) | 0.429 | 0.811 | 0.238 | 0.013 | −0.09 |
| Green class (GC) | 0.325 | 0.813 | 0.39 | −0.092 | −0.159 |
| Green combination (GP) | 0.209 | 0.816 | 0.093 | −0.154 | −0.064 |
| Green form (GF) | 0.576 | 0.421 | −0.36 | 0.455 | 0.167 |
| View method (GM) | 0.27 | 0.252 | 0.167 | −0.224 | 0.75 |
| Green color (GO) | −0.06 | 0.6 | 0.607 | −0.009 | −0.294 |
| Green situation (GS) | 0.399 | 0.266 | −0.381 | 0.427 | −0.376 |
| Plant trait (BF) | 0.235 | 0.576 | −0.482 | −0.343 | 0.163 |
| Plant luster (BL) | 0.724 | −0.26 | −0.058 | −0.241 | 0.224 |
| Seasonal ratio (SR) | 0.738 | −0.301 | 0.114 | −0.365 | 0.064 |
| Green visual ratio (GV) | 0.774 | −0.446 | 0.056 | −0.129 | −0.141 |
| Intervisibility (VA) | 0.832 | −0.285 | 0.327 | −0.054 | −0.206 |
| Green density (DC) | 0.708 | −0.045 | 0.428 | 0.21 | 0.027 |
| Green height (GH) | 0.81 | −0.449 | 0.185 | −0.116 | −0.082 |
| Oddity (ODD) | 0.693 | 0.27 | −0.548 | 0.257 | 0.087 |
| Awareness (ARE) | 0.082 | 0.143 | 0.301 | 0.673 | 0.426 |
| Ancient wood ratio (PAW) | 0.056 | −0.555 | 0.429 | 0.528 | 0.043 |
| Tree age (GAT) | 0.412 | −0.19 | −0.637 | 0.083 | −0.194 |

(5) Annotated street samples to be analyzed are input into the street greening quality detection model to obtain annotated results of street greening quality grading detection target data.

(5-1) Physiological data of J subjects with respect to I street greening images of N street samples are collected to obtain an initial greening quality variable matrix $Z=\{z_{ij}\}$, (i=1, 2, 3, ..., M; j=1, 2, 3, ..., N) of M greening quality variable factors of the N street samples, and the EEG, ECG, EDA and EMG physiological activation feature parameters of the N street samples are annotated in classes according to the classes of the greening quality variable factor indexes;

(5-2) A greening activation relationship fusion model among the physiological activation feature indexes is established through (3-3), and a fused greening activation index of the J subjects with respect to the street greening quality variable factors is generated, which are conducive to accurate recognition on the degrees of activation of the subjects with respect to different street greening within a sampling time point. Activation confidence is set within a [0, 1] interval, and the variable factors of the street samples are annotated with the activation degrees;

(5-3) Greening quality detection conditions are preset, the street greening quality is divided into four levels $G_1$, $G_2$, $G_3$, and $G_4$, and hierarchical values are assigned to the element dimensions of the street samples from high to low, to rank the greening quality of the street samples;

$$C_i = \begin{cases} 4, & x_{ij} \in [\bar{x}+0.5\sigma, x_{max}] \\ 3, & x_{ij} \in [\bar{x}, \bar{x}+0.5\sigma) \\ 2, & x_{ij} \in [\bar{x}-0.5\sigma, \bar{x}) \\ 1, & x_{ij} \in [x_{min}, \bar{x}-0.5\sigma) \end{cases}$$

where $x_{ij}$ represents greening activation annotation data of an $j^{th}$ element dimension at an $i^{th}$ location, x represents an average value of greening activation degrees of all samples, σ represents a standard deviation of the greening activation degrees of all samples, and $C_i$ represents a level of assigned greening quality of the $i^{th}$ element dimension; and (5-4) The annotated street samples are input into the street greening quality detection model, activation degrees of the element dimensions of the street samples are obtained one by one through the calculated greening variable factors and element dimensions, on this basis, the greening quality of each element dimension is reassigned with reference to the greening quality grading detection conditions, and weighted superposition is performed on the dimension weights of the greening quality elements to form and annotate dimensionless greening quality values of the street samples;

$$Y = \sum_{t=1}^{n} w_t^* C_t'$$

where Y represents the greening quality values of the street samples, $w_i^*$ represents a weight of a $i^{th}$ element dimension, and $C_i'$ represents level assignment of greening quality at the $i^{th}$ element dimension.

In this example, EEG, ECG, EDA, and EMG physiological data of 60 subjects with respect to greening images from 4 street sample locations are collected. According to the greening quality factor index system in (1-1), a plurality of greening activation feature parameters are fused to obtain greening activation index data of 18 variable factors and 4 element dimensions of the street samples. The greening quality values of the element dimension indexes of the samples are compared, counted, and annotated through latent principal component analysis, weighted superposition and greening quality grading detection, feasible improvement measures are provided for areas with abnormal indexes, and the greening quality statuses among the obtained street samples are ranked and compared (as shown in Table 5). The annotation results in this example are compared with the results obtained by testing with the previous greening quality detection model (4-4), showing that the matching rate reaches 86%.

TABLE 5

Degrees of activation and environmental quality of some street samples

| Element dimension | Wuhan Zhongshan Avenue | | Shanghai Xinhua Road | | Guangzhou Shamian Street | | Nanjing Zhongshan Road | |
|---|---|---|---|---|---|---|---|---|
| | Degree of activation | Assignment | Degree of activation | Assignment | Degree of activation | Assignment | Degree of activation | Assignment |
| Greening structure | 32.17 | 2 | 73.27 | 4 | 56.79 | 4 | 61.41 | 4 |
| Plant texture | 45.64 | 3 | 52.14 | 3 | 66.14 | 3 | 27.67 | 2 |
| Line of sight relationship | 33.45 | 2 | 53.45 | 3 | 42.74 | 3 | 56.78 | 3 |
| Landscape characteristics | 23.74 | 1 | 32.78 | 2 | 47.67 | 3 | 39.95 | 3 |
| Quality value | 2.0674 | | 3.0748 | | 3.2831 | | 3.0074 | |
| Rank | 4 | | 2 | | 1 | | 3 | |

Based on the same inventive concept, the present invention further provides a computer device. The computer device includes: one or more processors; and a memory, configured to store one or more computer programs. The programs include program instructions, and the processor is configured to execute the program instructions stored in the memory. The processor may be a central processing unit (CPU), or other general-purpose processors, digital signal processors (DSP), application specific integrated circuits (ASIC), field-programmable gate arrays (FPGA), or other programmable logic devices, discrete gates or transistor logic devices, discrete hardware components, etc. The processor is a computing core and a control core of a terminal, and is configured to implement one or more instructions, specifically to load and execute one or more instructions in a computer storage medium to implement the foregoing method.

It should be further explained that, based on the same inventive concept, the present invention further provides a computer storage medium storing a computer program that is executed by a processor to perform the foregoing method. The storage medium may be one of or any combination of more computer-readable media. The computer-readable medium may be a computer-readable signal medium or a computer-readable storage medium. The computer-readable storage medium may be, but is not limited to a system, apparatus, or device of electricity, magnetism, light, electricity, magnetism, infrared, or semiconductor, or any combination of the above. More specific examples of the computer-readable storage medium (non-exhaustive list) include: an electrical connections with one or more wires, a portable computer disk, a hard disk, a random access memory (RAM), a read-only memory (ROM), an erasable programmable read-only memory (EPROM or flash), an optical fiber, a portable compact disk read-only memory (CD-ROM), an optical storage device, a magnetic storage device, or any suitable combination of the above. In the present invention, the computer-readable storage medium may be any tangible medium including or storing a program, and the program may be used by or in combination with an instruction execution system, apparatus, or device.

In the description of this specification, the description with reference to the term "one embodiment", "example", "specific example", or the like means that a specific feature, structure, material, or characteristic described in conjunction with the embodiment or example is included in at least one embodiment or example of the present disclosure. In this specification, the schematic expression of the foregoing term does not necessarily refer to the same embodiment or example. Moreover, the described specific feature, structure, material, or characteristic can be combined in any one or more embodiments or examples in a suitable manner.

The above shows and describes the basic principles, main features, and advantages of the present disclosure. Those skilled in the art should be understood that the present disclosure is not limited to the foregoing embodiments. The descriptions in the foregoing embodiments and specification only illustrate the principles of the preset disclosure. The present disclosure has various changes and improvements without departing from the spirit and scope of the present disclosure, and these changes and improvements fall within the scope of protection of the present disclosure.

What is claimed is:

1. A street greening quality detection method based on a physiological activation recognition, comprising the following steps:
    establishing a greening quality factor index system according to high-frequency street landscape characteristics, and obtaining and uniformly processing street greening images for greening stimulus physiological experiments;
    collecting EEG, ECG, EDA and EMG raw data stimulated by the street greening images, and performing reclassification and differential wave processing on the raw data according to greening quality factor indexes to obtain valid physiological data that can be used for activation feature extraction of greening quality factors;
    calculating EEG, ECG, EDA and EMG physiological activation feature parameters of the greening quality factors according to the obtained valid physiological data, training the physiological activation feature parameters by transfer learning fusion to determine importance of physiological activation features, and recognizing weighted average greening activation indexes of the greening quality factors;
    analyzing weighted average greening activation index data of the greening quality factors to form a street greening quality detection model for contrast detection of street greening quality; and
    inputting annotated street samples to be analyzed into the street greening quality detection model to obtain annotated results of street greening quality grading detection target data.

2. The street greening quality detection method based on the physiological activation recognition according to claim 1, wherein the process of establishing the greening quality factor index system comprises the following steps:

collecting statistics on frequencies of street greening structures, plant attributes, visual landscape and the like, selecting high-frequency street greening quality factors, and sorting out constituent elements, typical features and environmental connotations of street greening by a theoretical analysis method, to establish the street greening quality factor index system, wherein the street greening quality factor index system comprises primary element dimensions, secondary variable factors and tertiary factor change form indexes;

acquiring data of built environment street view images, determining street greening scene class images in the street view images by location scene recognition technology, performing feature sampling on single greening quality variable factors of the greening scene class images by image element semantic segmentation technology, and determining clear street greening target images by a square gradient function; and randomly selecting m street greening images from the street greening target images, and performing three phase randomizations on the m street greening images to obtain 3*m random phase images and form an experimental stimulus image library; dividing all experimental stimulus images in the experimental stimulus image library into n groups through inter-group experiments, and playing the experimental stimulus images at a random inter-group and same frequency in a laboratory environment to obtain EEG, ECG, EDA, EMG and trigger signals of corresponding data segments of the images in real time.

3. The street greening quality detection method based on the physiological activation recognition according to claim 2, wherein primary element dimension indexes of the greening quality factor index system comprise greening structure, plant texture, line of sight relationship, and landscape characteristics; the secondary variable factor indexes are extensions of primary greening quality elements; and the tertiary factor change form indexes are manifestations of variable factors, and factor features of greening quality are sampled through the built environment street view images.

4. The street greening quality detection method based on the physiological activation recognition according to claim 1, wherein the process of collecting the EEG, ECG, EDA and EMG raw data stimulated by the street greening images, and performing the reclassification and differential wave processing on the raw data according to the greening quality factor indexes comprises the following steps:

capturing raw data of each street greening target image when stimulated, and classifying raw data segments representing a same greening quality variable factor into one class according to markers recorded by trigger signals, wherein each class of data segments reflects EEG, ECG, EDA and EMG changes of subjects under an influence of a variable factor; performing baseline correction, bandpass filtering, average reference processing, ICA, noise reduction and artifact removal on the raw data segments, and correcting signal offsets by EMD, so as to solve average amplitudes and differential waves of non-stimulus state electrical signals caused by greening quality factor stimulus states; and analyzing amplitudes and phase images of differential waveforms by Hanning windowing, fast Fourier transform and wavelet transform, and extracting β and α frequency bands of five EEG differential wave leads PZ, P4, P5, O1, OZ, and O2, low-frequency and high-frequency bands of ECG differential waves at R-R intervals, high-frequency bands of EMG differential waves after full-wave rectification, and a normalized conductivity GSR of EDA differential waves within an exposure time window of the street greening target images, so as to calculate power spectral densities of the EEG, ECG and EMG frequency bands and a first-order difference of the EDA conductivity, to obtain valid physiological data for physiological activation feature recognition of the greening quality factors.

5. The street greening quality detection method based on the physiological activation recognition according to claim 1, wherein the process of calculating the EEG, ECG, EDA and EMG physiological activation feature parameters of the greening quality factors according to the obtained valid physiological data, training the physiological activation feature parameters by the transfer learning fusion to determine the importance of the physiological activation features, and recognizing the weighted average greening activation indexes of the greening quality factors comprises the following steps:

superposing and averaging physiological data of each class of greening quality factors according to the obtained valid physiological data, calculating the EEG, ECG, EDA and EMG physiological activation feature parameters of the greening quality factors respectively, and normalizing the calculated EEG, ECG, EDA and EMG physiological activation feature parameters of the greening quality factors;

obtaining a physiological activation feature vector $A^{(m)}=\{a_x^{(m)}\}$, ($x=1, 2, \ldots, N$, $m=1, 2, \ldots, J$) of the greening quality factors from the normalized EEG, ECG, EDA and EMG physiological activation feature parameters of the greening quality factors, wherein $a_i^{(m)}$ represents an $m^{th}$ physiological activation feature of an $x^{th}$ class of greening quality factor objects; constructing a physiological activation feature importance determination matrix $B=\{b_{ij}\}$, wherein $b_{ij}$ represents an importance degree ratio of an $i^{th}$ activation feature dimension to an $j^{th}$ activation feature dimension; consequently, obtaining a weight vector $w^*=[w_1, w_2 \ldots, w_j]$ of each feature; and fusing the physiological activation features by transfer learning TLDA, using 70% of the samples as a source domain dataset and remaining 30% as a target domain dataset, obtaining marker activation values of source domain street greening target images, performing sparse self-encoding on the physiological activation feature vector $A^{(m)}$ and the marker activation value Y of the greening quality factors, determining the number of neurons q (q<m) in a self-encoder, introducing $A^{(m)}$ into a neural network, and assigning physiological activation feature weights after neural network training to obtain an ensemble vector E of fused features and a weighted average greening activation index O corresponding to E, as follows:

$$O = \frac{1}{4}\sum_{i=1}^{m}\frac{\omega_i}{\sum_{j=1}^{m}\omega_j}o_k$$

wherein $\omega_i$ represents a weight of each source domain, namely, a modulus of a similarity vector in the ensemble vector E, and $o_k$ represents a predicted activation degree of a $k^{th}$ class of greening quality factors.

6. The street greening quality detection method based on the physiological activation recognition according to claim 5, wherein the process of calculating the EEG, ECG, EDA and EMG physiological activation feature parameters of the greening quality factors comprises the following steps:

calculating an EEG activation feature parameter $A_{EEG}$ of a greening factor object by the following formula:

$$A_{EEG} = \frac{P_{\beta,x}}{P_{\alpha,x}}$$

wherein $P_{\beta,x}$ and $P_{\alpha,x}$ represent relative average power of the five leads PZ, P4, P5, O1, OZ, and O2 with respect to $\beta$ and $\alpha$ bands of a currently calculated greening quality factor object x;

calculating an ECG activation feature parameter $A_{ECG}$ of the greening factor object by the following formula:

$$A_{ECG} = \frac{P_{LF,x}}{P_{HF,x}}$$

wherein $P_{LF,x}$ represents a power value of an ECG low-frequency component of the greening quality factor x, and $P_{HF,x}$ represents a power value of an ECG high-frequency component of the greening quality factor x;

calculating an EDA activation feature parameter $A_{EDA}$ of the greening factor object by the following formula:

$$A_{EDA} = \frac{1}{2}(t_{peak} - t_{onset}) * (s_{peak} - s_{onset})$$

wherein $t_{peak}$ and $t_{onset}$ represent a peak and beginning of $\Delta$GSR rise time during stress response, $s_{peak}$ and $s_{onset}$ represent a peak and beginning of a $\Delta$GSR amplitude value during stress response, and ADA represents activation of 10% higher than a baseline during GSR stress response;

calculating an EMG activation feature parameter $A_{EMG}$ of the greening factor object by the following formula:

$$A_{EMG} = \frac{1}{2}\int_0^{+\infty} P_{EMG,x} df$$

wherein $P_{EMG,x}$ represents a power spectral density function of EMG signals of the currently calculated greening quality factor object x, and f represents a frequency of the EMG signals; and normalizing the physiological activation feature parameters of each greening quality factor and introducing the following calculation formula:

$$A_{Normalized} = \left(\frac{A(i) - A_{min}}{A_{max} - A_{min}}\right) \times 100$$

wherein $A(i)$ represents an $i^{th}$ activation feature parameter, $A_{min}$ and $A_{max}$ represent a minimum value and a maximum value of the activation feature parameters, and $A_{Normalized}$ represents normalized activation feature parameters.

7. The street greening quality detection method based on the physiological activation recognition according to claim 1, wherein the process of analyzing the weighted average greening activation index data of the greening quality factors to form the street greening quality detection model comprises the following steps:

obtaining a weighted average greening activation index of each class of greening quality factors, checking the weighted average greening activation index data of the greening quality factors by KMO measure of sampling adequacy and Bartlett's test of sphericity, wherein when KMO value >0.6 and sphericity test adjoint probability P value≤0.01, it is considered that factor variables are strongly correlated and are suitable for further analysis on greening factor objects;

calculating a cumulative variance contribution rate $M_K$ of latent principal components of an initial greening quality variable matrix $X=\{x_{ij}\}$, (i=1, 2, 3, ..., m; j=1, 2, 3, ..., n), and selecting latent principal components of greening quality at $M_K \geq 80\%$ as follows:

$$M_K = \sum_{i=1}^{k} \frac{\varepsilon_{ij}}{\sqrt{\eta_j}}$$

wherein $x_{ij}$ represents a $j^{th}$ greening quality variable factor of an $i^{th}$ sample; $\varepsilon_{ij}/\sqrt{\eta_j}$ represents a $k^{th}$ latent principal component of the greening quality, $\varepsilon_{ij}$ represents factor load of a $j^{th}$ latent principal component of an $i^{th}$ variable factor, and $n_{ij}$ represents a characteristic root of the $j^{th}$ latent principal component;

extracting first k latent principal components to detect the street greening quality, and calculating a weight $w_i'$ of a single greening quality variable factor according to the related coefficient matrices and the variance contribution rate as follows:

$$w_i' = \left|\sum_{i=1}^{k}\left(\frac{\varepsilon_{ij}}{\sqrt{\eta_j}} * \gamma_j\right)\right|/\gamma_j$$

wherein $\gamma_j$ represents a variance contribution rate corresponding to the $j^{th}$ latent principal component of the greening quality, and the larger the $w_i'$, the greater the importance of the greening quality variable factor; and forming the street greening quality detection model according to weight coefficients of the greening quality variable factors, which is used for contrast detection of the street greening quality:

$$G = \lambda_1 x_1 + \lambda_2 x_3 + \lambda_3 x_3 + \ldots + \lambda_j x_j$$

wherein $\lambda_1$ represents an influence coefficient of the $i^{th}$ factor, and $x_j$ represents greening activation index data of a $j^{th}$ re-extracted factor.

8. The street greening quality detection method based on the physiological activation recognition according to claim 1, wherein the process of inputting the annotated street samples to be analyzed into the street greening quality detection model to obtain the annotated results of the street greening quality grading detection target data comprises the following steps:

collecting physiological data of J subjects with respect to I street greening images of N street samples to obtain an initial greening quality variable matrix $Z=\{z_{ij}\}$, (i=1, 2, 3, ..., M; j=1, 2, 3, ..., N) of M greening quality variable factors of the N street samples, and annotating the EEG, ECG, EDA and EMG physiological activation feature parameters of the N street samples in classes according to the classes of the greening quality variable factor indexes;

establishing a greening activation relationship fusion model among the EEG, ECG, EDA and EMG activation feature parameters, generating a fused greening activation index of the J subjects with respect to the street greening quality variable factors, setting confidence of the greening activation index data within a [0, 1] interval, and annotating the variable factors of the street samples with activation degrees;

presetting greening quality detection conditions, dividing the street greening quality into four levels $G_1$, $G_2$, $G_3$, and $G_4$, and assigning hierarchical values to element dimensions of the street samples from high to low, to rank the greening quality of the street samples;

$$C_i = \begin{cases} 4, x_{ij} \in [\bar{x} + 0.5\sigma, x_{max}] \\ 3, x_{ij} \in [\bar{x}, \bar{x} + 0.5\sigma) \\ 2, x_{ij} \in [\bar{x} - 0.5\sigma, \bar{x}) \\ 1, x_{ij} \in [x_{min}, \bar{x} - 0.5\sigma) \end{cases}$$

wherein $x_{ij}$ represents greening activation annotation data of an $j^{th}$ element dimension at an $i^{th}$ location, $\bar{x}$ represents an average value of greening activation degrees of all samples, $\sigma$ represents a standard deviation of the greening activation degrees of all samples, and $C_j$ represents a level of assigned greening quality of an $i^{th}$ element dimension; and inputting the annotated street samples into the street greening quality detection model, obtaining activation degrees of the element dimensions of the street samples one by one through the calculated greening variable factors and element dimensions, on this basis, reassigning the greening quality of each element dimension with reference to the greening quality grading detection conditions, and performing weighted superposition on dimension weights of the greening quality elements to form and annotate dimensionless greening quality values of the street samples;

$$Y = \sum_{t=1}^{n} w_t^* C_t'$$

wherein Y represents the greening quality values of the street samples, $w_i^*$ represents a weight of a $i^{th}$ element dimension, and $C_i'$ represents level assignment of greening quality at the $i^{th}$ element dimension.

9. A device, comprising:
one or more processors; and
a memory, configured to store one or more programs, wherein
when the one or more programs are executed by the one or more processors, the one or more processors are enabled to implement the street greening quality detection method based on the physiological activation recognition according to claim 1.

10. The device according to claim 9, wherein in the street greening quality detection method, the process of establishing the greening quality factor index system comprises the following steps:

collecting statistics on frequencies of street greening structures, plant attributes, visual landscape and the like, selecting high-frequency street greening quality factors, and sorting out constituent elements, typical features and environmental connotations of street greening by a theoretical analysis method, to establish the street greening quality factor index system, wherein the street greening quality factor index system comprises primary element dimensions, secondary variable factors and tertiary factor change form indexes;

acquiring data of built environment street view images, determining street greening scene class images in the street view images by location scene recognition technology, performing feature sampling on single greening quality variable factors of the greening scene class images by image element semantic segmentation technology, and determining clear street greening target images by a square gradient function; and randomly selecting m street greening images from the street greening target images, and performing three phase randomizations on the m street greening images to obtain 3*m random phase images and form an experimental stimulus image library; dividing all experimental stimulus images in the experimental stimulus image library into n groups through inter-group experiments, and playing the experimental stimulus images at a random inter-group and same frequency in a laboratory environment to obtain EEG, ECG, EDA, EMG and trigger signals of corresponding data segments of the images in real time.

11. The device according to claim 10, wherein in the street greening quality detection method, primary element dimension indexes of the greening quality factor index system comprise greening structure, plant texture, line of sight relationship, and landscape characteristics; the secondary variable factor indexes are extensions of primary greening quality elements; and the tertiary factor change form indexes are manifestations of variable factors, and factor features of greening quality are sampled through the built environment street view images.

12. The device according to claim 9, wherein in the street greening quality detection method, the process of collecting the EEG, ECG, EDA and EMG raw data stimulated by the street greening images, and performing the reclassification and differential wave processing on the raw data according to the greening quality factor indexes comprises the following steps:

capturing raw data of each street greening target image when stimulated, and classifying raw data segments representing a same greening quality variable factor into one class according to markers recorded by trigger signals, wherein each class of data segments reflects EEG, ECG, EDA and EMG changes of subjects under an influence of a variable factor; performing baseline correction, bandpass filtering, average reference processing, ICA, noise reduction and artifact removal on the raw data segments, and correcting signal offsets by EMD, so as to solve average amplitudes and differential waves of non-stimulus state electrical signals caused by greening quality factor stimulus states; and analyzing amplitudes and phase images of differential waveforms by Hanning windowing, fast Fourier transform and wavelet transform, and extracting β and α frequency bands of five EEG differential wave leads PZ, P4, P5, O1, OZ, and O2, low-frequency and high-frequency bands of ECG differential waves at R-R intervals, high-frequency bands of EMG differential waves after full-wave rectification, and a normalized conductivity GSR of EDA differential waves within an exposure time window of the street greening target images, so as to calculate power spectral densities of the EEG, ECG and EMG frequency bands and a first-order difference of the EDA conductivity, to obtain valid physiological data for physiological activation feature recognition of the greening quality factors.

13. The device according to claim 9, wherein in the street greening quality detection method, the process of calculating the EEG, ECG, EDA and EMG physiological activation feature parameters of the greening quality factors according to the obtained valid physiological data, training the physiological activation feature parameters by the transfer learning fusion to determine the importance of the physiological activation features, and recognizing the weighted average greening activation indexes of the greening quality factors comprises the following steps:

superposing and averaging physiological data of each class of greening quality factors according to the obtained valid physiological data, calculating the EEG, ECG, EDA and EMG physiological activation feature parameters of the greening quality factors respectively, and normalizing the calculated EEG, ECG, EDA and EMG physiological activation feature parameters of the greening quality factors;

obtaining a physiological activation feature vector $A^{(m)}=\{a_x^{(m)}\}$, (x=1, 2, ..., N, m=1, 2, ..., J) of the greening quality factors from the normalized EEG, ECG, EDA and EMG physiological activation feature parameters of the greening quality factors, wherein $a_i^{(m)}$ represents an $m^{th}$ physiological activation feature of an $x^{th}$ class of greening quality factor objects; constructing a physiological activation feature importance determination matrix $B=\{b_{ij}\}$, wherein $b_{ij}$ represents an importance degree ratio of an $i^{th}$ activation feature dimension to an $j^{th}$ activation feature dimension; consequently, obtaining a weight vector $w^*=[w_1, w_2 ..., w_j]$ of each feature; and fusing the physiological activation features by transfer learning TLDA, using 70% of the samples as a source domain dataset and remaining 30% as a target domain dataset, obtaining marker activation values of source domain street greening target images, performing sparse self-encoding on the physiological activation feature vector $A^{(m)}$ and the marker activation value Y of the greening quality factors, determining the number of neurons q (q<m) in a self-encoder, introducing $A^{(m)}$ into a neural network, and assigning physiological activation feature weights after neural network training to obtain an ensemble vector E of fused features and a weighted average greening activation index O corresponding to E, as follows:

$$O = \frac{1}{4}\sum_{i=1}^{m}\frac{\omega_i}{\sum_{j=1}^{m}\omega_j}o_k$$

wherein $\omega_i$ represents a weight of each source domain, namely, a modulus of a similarity vector in the ensemble vector E, and $o_k$ represents a predicted activation degree of a $k^{th}$ class of greening quality factors.

14. The device according to claim 13, wherein in the street greening quality detection method, the process of calculating the EEG, ECG, EDA and EMG physiological activation feature parameters of the greening quality factors comprises the following steps:

calculating an EEG activation feature parameter $A_{EEG}$ of a greening factor object by the following formula:

$$A_{EEG} = \frac{P_{\beta,x}}{P_{\alpha,x}}$$

wherein $P_{\beta,x}$ and $P_{\alpha,x}$ represent relative average power of the five leads PZ, P4, P5, O1, OZ, and O2 with respect to $\beta$ and $\alpha$ bands of a currently calculated greening quality factor object x;

calculating an ECG activation feature parameter $A_{ECG}$ of the greening factor object by the following formula:

$$A_{ECG} = \frac{P_{LF,x}}{P_{HF,x}}$$

wherein $P_{LF,x}$ represents a power value of an ECG low-frequency component of the greening quality factor x, and $P_{HF,x}$ represents a power value of an ECG high-frequency component of the greening quality factor x;

calculating an EDA activation feature parameter $A_{EDA}$ of the greening factor object by the following formula:

$$A_{EDA} = \frac{1}{2}(t_{peak} - t_{onset}) * (s_{peak} - s_{onset})$$

wherein $t_{peak}$ and $t_{onset}$ represent a peak and beginning of $\Delta$GSR rise time during stress response, $s_{peak}$ and $s_{onset}$ represent a peak and beginning of a $\Delta$GSR amplitude value during stress response, and $A_{EDA}$ represents activation of 10% higher than a baseline during GSR stress response;

calculating an EMG activation feature parameter $A_{EMG}$ of the greening factor object by the following formula:

$$A_{EMG} = \frac{1}{2}\int_0^{+\infty} P_{EMG,x} df$$

wherein $P_{EMG,x}$ represents a power spectral density function of EMG signals of the currently calculated greening quality factor object x, and f represents a frequency of the EMG signals; and normalizing the physiological activation feature parameters of each greening quality factor and introducing the following calculation formula:

$$A_{Normalized} = \left(\frac{A(i) - A_{min}}{A_{max} - A_{min}}\right) \times 100$$

wherein A(i) represents an $i^{th}$ activation feature parameter, $A_{min}$ and $A_{max}$ represent a minimum value and a maximum value of the activation feature parameters, and $A_{Normalized}$ represents normalized activation feature parameters.

15. The device according to claim 9, wherein in the street greening quality detection method, the process of analyzing the weighted average greening activation index data of the greening quality factors to form the street greening quality detection model comprises the following steps:
  obtaining a weighted average greening activation index of each class of greening quality factors, checking the weighted average greening activation index data of the greening quality factors by KMO measure of sampling adequacy and Bartlett's test of sphericity, wherein when KMO value >0.6 and sphericity test adjoint probability P value≤0.01, it is considered that factor variables are strongly correlated and are suitable for further analysis on greening factor objects;
  calculating a cumulative variance contribution rate $M_K$ of latent principal components of an initial greening quality variable matrix $X=\{x_{ij}\}$, (i=1, 2, 3, ..., m; j=1, 2, 3, ..., n), and selecting latent principal components of greening quality at $M_K \geq 80\%$ as follows:

$$M_K = \sum_{i=1}^{k} \frac{\varepsilon_{ij}}{\sqrt{\eta_j}}$$

wherein $x_{ij}$ represents a $j^{th}$ greening quality variable factor of an $i^{th}$ sample; $\varepsilon_{ij}/\sqrt{\eta_j}$ represents a $k^{th}$ latent principal component of the greening quality, $\varepsilon_{ij}$ represents factor load of a $j^{th}$ latent principal component of an $i^{th}$ variable factor, and $\eta_{ij}$ represents a characteristic root of the $j^{th}$ latent principal component;
  extracting first k latent principal components to detect the street greening quality, and calculating a weight $w_i'$ of a single greening quality variable factor according to the related coefficient matrices and the variance contribution rate as follows:

$$w_i' = \left| \sum_{i=1}^{k} \left( \frac{\varepsilon_{ij}}{\sqrt{\eta_j}} * \gamma_j \right) \right| / \gamma_j$$

wherein $\gamma_j$ represents a variance contribution rate corresponding to the $j^{th}$ latent principal component of the greening quality, and the larger the $w_i'$, the greater the importance of the greening quality variable factor; and
  forming the street greening quality detection model according to weight coefficients of the greening quality variable factors, which is used for contrast detection of the street greening quality:

$$G = \lambda_1 x_1 + \lambda_2 x_2 + \lambda_3 x_3 + \ldots + \lambda_j x_j$$

wherein $\lambda_1$ represents an influence coefficient of the $i^{th}$ factor, and $x_j$ represents greening activation index data of a $j^{th}$ re-extracted factor.

16. The device according to claim 9, wherein in the street greening quality detection method, the process of inputting the annotated street samples to be analyzed into the street greening quality detection model to obtain the annotated results of the street greening quality grading detection target data comprises the following steps:
  collecting physiological data of J subjects with respect to I street greening images of N street samples to obtain an initial greening quality variable matrix $Z=\{z_{ij}\}$, (i=1, 2, 3, ..., M; j=1, 2, 3, ..., N) of M greening quality variable factors of the N street samples, and annotating the EEG, ECG, EDA and EMG physiological activation feature parameters of the N street samples in classes according to the classes of the greening quality variable factor indexes;
  establishing a greening activation relationship fusion model among the EEG, ECG, EDA and EMG activation feature parameters, generating a fused greening activation index of the J subjects with respect to the street greening quality variable factors, setting confidence of the greening activation index data within a [0, 1] interval, and annotating the variable factors of the street samples with activation degrees;
  presetting greening quality detection conditions, dividing the street greening quality into four levels $G_1$, $G_2$, $G_3$, and $G_4$, and assigning hierarchical values to element dimensions of the street samples from high to low, to rank the greening quality of the street samples;

$$C_i = \begin{cases} 4, & x_{ij} \in [\bar{x} + 0.5\sigma, x_{max}] \\ 3, & x_{ij} \in [\bar{x}, \bar{x} + 0.5\sigma) \\ 2, & x_{ij} \in [\bar{x} - 0.5\sigma, \bar{x}) \\ 1, & x_{ij} \in [x_{min}, \bar{x} - 0.5\sigma) \end{cases}$$

wherein $x_{ij}$ represents greening activation annotation data of an $j^{th}$ element dimension at an $i^{th}$ location, $\bar{x}$ represents an average value of greening activation degrees of all samples, $\sigma$ represents a standard deviation of the greening activation degrees of all samples, and $C_i$ represents a level of assigned greening quality of an $i^{th}$ element dimension; and
  inputting the annotated street samples into the street greening quality detection model, obtaining activation degrees of the element dimensions of the street samples one by one through the calculated greening variable factors and element dimensions, on this basis, reassigning the greening quality of each element dimension with reference to the greening quality grading detection conditions, and performing weighted superposition on dimension weights of the greening quality elements to form and annotate dimensionless greening quality values of the street samples;

$$Y = \sum_{t=1}^{n} w_t^* C_t'$$

wherein Y represents the greening quality values of the street samples, $w_i^*$ represents a weight of a $i^{th}$ element dimension, and $C_i'$ represents level assignment of greening quality at the $i^{th}$ element dimension.

17. A storage medium comprising computer executable instructions, wherein the computer executable instructions are used to perform the street greening quality detection method based on the physiological activation recognition according to claim 1 when executed by a computer processor.

18. The storage medium according to claim 17, wherein in the street greening quality detection method, the process of establishing the greening quality factor index system comprises the following steps:
  collecting statistics on frequencies of street greening structures, plant attributes, visual landscape and the like, selecting high-frequency street greening quality factors, and sorting out constituent elements, typical features and environmental connotations of street greening by a theoretical analysis method, to establish the street greening quality factor index system, wherein the street greening quality factor index system comprises primary element dimensions, secondary variable factors and tertiary factor change form indexes;

acquiring data of built environment street view images, determining street greening scene class images in the street view images by location scene recognition technology, performing feature sampling on single greening quality variable factors of the greening scene class images by image element semantic segmentation technology, and determining clear street greening target images by a square gradient function; and randomly selecting m street greening images from the street greening target images, and performing three phase randomizations on the m street greening images to obtain 3*m random phase images and form an experimental stimulus image library; dividing all experimental stimulus images in the experimental stimulus image library into n groups through inter-group experiments, and playing the experimental stimulus images at a random inter-group and same frequency in a laboratory environment to obtain EEG, ECG, EDA, EMG and trigger signals of corresponding data segments of the images in real time.

19. The storage medium according to claim 18, wherein in the street greening quality detection method, primary element dimension indexes of the greening quality factor index system comprise greening structure, plant texture, line of sight relationship, and landscape characteristics; the secondary variable factor indexes are extensions of primary greening quality elements; and the tertiary factor change form indexes are manifestations of variable factors, and factor features of greening quality are sampled through the built environment street view images.

20. The storage medium according to claim 17, wherein in the street greening quality detection method, the process of collecting the EEG, ECG, EDA and EMG raw data stimulated by the street greening images, and performing the reclassification and differential wave processing on the raw data according to the greening quality factor indexes comprises the following steps:

capturing raw data of each street greening target image when stimulated, and classifying raw data segments representing a same greening quality variable factor into one class according to markers recorded by trigger signals, wherein each class of data segments reflects EEG, ECG, EDA and EMG changes of subjects under an influence of a variable factor; performing baseline correction, bandpass filtering, average reference processing, ICA, noise reduction and artifact removal on the raw data segments, and correcting signal offsets by EMD, so as to solve average amplitudes and differential waves of non-stimulus state electrical signals caused by greening quality factor stimulus states; and analyzing amplitudes and phase images of differential waveforms by Hanning windowing, fast Fourier transform and wavelet transform, and extracting $\beta$ and $\alpha$ frequency bands of five EEG differential wave leads PZ, P4, P5, O1, OZ, and O2, low-frequency and high-frequency bands of ECG differential waves at R-R intervals, high-frequency bands of EMG differential waves after full-wave rectification, and a normalized conductivity GSR of EDA differential waves within an exposure time window of the street greening target images, so as to calculate power spectral densities of the EEG, ECG and EMG frequency bands and a first-order difference of the EDA conductivity, to obtain valid physiological data for physiological activation feature recognition of the greening quality factors.

* * * * *